US005767080A

United States Patent [19]
Beck et al.

[11] Patent Number: 5,767,080
[45] Date of Patent: Jun. 16, 1998

[54] ENHANCED MILK PRODUCTION IN DAIRY CATTLE

[75] Inventors: James F. Beck, Marshall, Mich.; Dale H. Storck, Sugar Grove, Ill.; David P. Casper, Elk River, Minn.

[73] Assignee: Cargill, Incorporated, Wayzata, Minn.

[21] Appl. No.: 795,549

[22] Filed: Feb. 6, 1997

Related U.S. Application Data

[63] Continuation-in-part of Ser. No. 699,560, Aug. 19, 1996, which is a continuation-in-part of Ser. No. 641,486, May 1, 1996.

[51] Int. Cl.$^6$ .............................. A61K 38/27; A23C 7/00; A23K 1/00
[52] U.S. Cl. ................................ 514/12; 119/174; 800/235
[58] Field of Search ............................. 514/12; 119/174; 800/235

[56] References Cited

U.S. PATENT DOCUMENTS

| | | | |
|---|---|---|---|
| 4,693,973 | 9/1987 | Buell. | |
| 4,977,140 | 12/1990 | Ferguson et al. | |
| 5,013,713 | 5/1991 | Mitchell. | |
| 5,037,806 | 8/1991 | Krivi. | |
| 5,086,041 | 2/1992 | Mitchell. | |
| 5,145,695 | 9/1992 | Smith et al. | 426/2 |
| 5,156,851 | 10/1992 | Castillo et al. | |
| 5,219,596 | 6/1993 | Smith et al. | 426/2 |
| 5,411,951 | 5/1995 | Mitchell. | |
| 5,474,980 | 12/1995 | Mitchell. | |

OTHER PUBLICATIONS

Barriere et al., *Brown-midrib genes of maize: a review*, Agronomie (1993) 13, pp. 865–876.
Block et al., *Brown midrib-3 Corn Silage and Heat Extruded Soybeans for Early Lactating Dairy Cows*, JDSCAE 64 (9) 1813–1825 (1981).
Weller et al., *The feeding value of normal and brown midrib-3 maize silage*, J. Agric. Sci., Camb. (1986) 106, pp. 31–35.
Keith et al., *Nutritional Value of Brown Midrib Corn Silage for Lactating Dairy Cows*, J. Dairy Sci., (1979) 62:788–792.
Stallings et al., *In Vivo Evaluation of Brown-Midrib Corn Silage by Sheep and Lactating Dairy Cows*, (1982) J. Dairy Sci., 65:1945–1949.
Grant et al., *Brown Midrib Sorghum Silage for Midlactation Dairy Cows*, (1995) J. Dairy Sci., 78:1970–1980.
Sommerfeldt et al., *Brown-Midrib Corn Silage for Lactating Dairy Cows*, (1979) J. Dairy Sci., 62:1611–1618.
Barriere et al., *Characteristics of the Bm3 corn genotypes in the climate of southwestern France*, English translation of "Bull. Tech. C.R./..V., Theix. I.N.R.A. 19×5 (60) 43–58".
Frenchick et al., *Brown Midrib Corn Silage in Dairy Cattle Rations*, JDSCAE 59(12) 2126–2129 (1976).
Goering et al., *Forage Fiber Analyses (Apparatus, Reagents, procedures, and Some Applications)*, Agriculture Handbook 379, (1970) 1–20.
Rook et al., *Intake and Digestibility of Brown-Midrib Corn Silage by Lactating Dairy Cows*, (1977) J. Dairy Sci., 60:1894–1904.
Lechtenberg et al., *Laboratory and in vitro Evaluation of Inbred and $F_2$ Population of Brown Midrib Mutants of Zea mays L.* (1972) Agron. J. 64:657–660.
Winsryg et al., "Effect of Sometribove on Rumen Fermentation, Rate of Passage, Digestibility, and Milk Production Responses in Dairy Cows", *J. Dairy Sci.*, 74:3518–3523 (1991).
Austin et al., "Influence of Bovine Somatropin and Nutrition on Production and Composition of Milk from Dairy Cows," *J. Dairy Sci.*, 74:3290–3932 (1991).
Miller et al., "Relationship of Early Lactation and Bovine Somatotropin on Nutrient Uptake by Cow Mammary Glands," *J. Dairy Sci.*, 74:3800–3806 (1991).
Allen et al., "Fiber Digestibility of Forages." Presented at the 1996 Minnesota Nutrition Conference, Bloomington, MN, Sep. 24–25, 1996.

*Primary Examiner*—Mary E. Mosher
*Attorney, Agent, or Firm*—Fish & Richardson P.C., P.A.

[57] ABSTRACT

A method for enhancing milk production in dairy cows is disclosed herein. The method comprises feeding dairy cows a feed ration comprising silage made from corn plants that are homozygous for at least one bm gene and, coextensively in time, administering biologically active somatotropin to the cows.

19 Claims, 1 Drawing Sheet

ENHANCED MILK PRODUCTION IN DAIRY CATTLE

This is a continuation-in-part of U.S. patent application Ser. No. 08/699,560, filed Aug. 19, 1996, which is a continuation-in-part of U.S. patent application Ser. No. 08/641,486, filed May 1, 1996.

FIELD OF THE INVENTION

This invention relates to increasing milk production in dairy cows. More particularly the invention relates to increasing milk production in dairy cows by feeding a ration comprising silage from corn plants exhibiting the brown midrib phenotype and also administering an effective amount of a biologically active somatotropin.

BACKGROUND OF THE INVENTION

Corn plants (*Zea mays* L.) are bred by both self-pollination and cross-pollination techniques. Corn is a monoecious plant, i.e., each plant has separate male and female flowers on the same plant, located on the tassel and ear, respectively. Natural pollination occurs in corn when pollen is shed from tassels and contacts silks of the same plant or a different plant that protrude from tops of the developing ears. Methods and techniques for the development of inbred corn lines and hybrid corn varieties are known in the art. Hallauer, A., Maize, in Principles of Cultivar Development, Vol. 2, Fehr, W. ed. pp. 249–294, Macmillan, New York, (1987). Currently, many hybrid corn varieties are produced by crossing two inbred lines to produce $F_1$ hybrid progeny. The $F_1$ plants exhibit heterosis, or hybrid vigor, resulting in plants having high yield and superior agronomic performance in the hybrid combination. The production and development of inbred corn lines and hybrid corn varieties are discussed in, for example, U.S. Pat. Nos. 5,367,109 and 5,495,067, which are incorporated herein by reference.

Research studies on maize have resulted in the identification of numerous genetic loci. See, e.g., the maize genetic database on the Worldwide Web at http://teosinte.agron.missour.edu/top.html.

To supply needed nutrients for increased milk production by lactating dairy cattle is an ongoing challenge facing the dairy industry. This challenge is complicated by the fact that, even though a dairy cow's diet may meet the National Research Council recommended nutrient requirements, the diet may still lack some nutrients at increased levels required for higher milk production. One reason for this difficulty in meeting nutrient requirements is the complexity of the digestive system of ruminants such as dairy cattle.

In cattle, ingested feed first passes into the reticulorumen, where it is subject to anaerobic microbial fermentation. Microbial fermentation begins the digestive process and gives a ruminant the ability to utilize fibrous feeds, in contrast to monogastric animals. Ruminants meet their nutrient needs by utilizing the by-products of microbial fermentation, along with any undigested feed residues and the resultant microbial mass that passes from the rumen.

Anaerobic microbial fermentation is an advantage to ruminants because it allows them to benefit from feeds which cannot be utilized by non-ruminants. However, microbial activity limits the ability to provide supplemental nutrients to a ruminant animal, because many desirable nutrients, such as proteins, amino acids and digestible fiber, will be metabolized by microbes before the nutrients reach a site where they can be absorbed and utilized by the ruminant.

Attempts have been made to increase milk production in dairy cattle by manipulating the feed ration. For example, rations containing silage derived from corn plants carrying a brown midrib (bm) mutation have been fed to cattle. Stallings, C. et al., J. Dairy Sci., 65:1945–1949 (1982); Block, E. et al., J. Dairy Sci. 64:1813–1825 (1981); Keith, E. et al., J. Dairy Sci. 62:788 (1979). The bm gene decreases and alters the lignin content in the vegetative parts of such corn plants; silage made from such plants has increased fiber digestibility compared to silage from corn plants not exhibiting the brown midrib phenotype. In general, these studies indicated that there was no increase in milk production in cows fed silage from bm corn. It was concluded that the cows fed a diet containing bm silage generally partitioned the nutrients into meat or fat body tissues rather than milk production. Barriere et al., Agronomie 13:865–876 (1993).

Attempts have been made to increase the efficiency of feed utilization and milk production by using various formulations and feed supplements. Despite continued improvement in the development of dairy cattle feed rations, it is desirable to further increase the efficiency of feed utilization and milk production by dairy cattle.

SUMMARY OF THE INVENTION

A method for enhancing milk production in a dairy cow is disclosed herein. The method comprises the steps of feeding to the cow, during a selected period, a total dairy cattle feed ration in conjunction with the delivery of an effective amount of a biologically active somatotropin to the cow.

The feed ration comprises a combination of a forage component and a feed composition. The forage component comprises from about 20% to about 60% of the ration and has from about 20% to about 100% corn silage produced from $F_1$ hybrid corn plants homozygous for bm3. The silage has an in vitro neutral detergent fiber digestibility of about 44% to about 60%. The ration has a fiber content of about 20% to about 40% and a crude protein content of from about 17% to about 21% on a dry matter basis. About 30% to about 50% of the crude protein is soluble protein.

In certain embodiments, the neutral detergent fiber digestibility is from about 6 percent to about 15 percent greater than the neutral detergent fiber digestibility of isogenic normal corn silage.

In some embodiments, the forage component comprises from about 40% to about 60% of the ration, and the bm3 corn silage comprises from about 40% to about 80% of the forage component. In some embodiments, the forage component comprises from about 45% to about 55% of the ration and the bm3 corn silage comprises from about 50% to about 80% of the forage component.

The biologically active somatotropin is administered to the cow under conditions delivering an effective amount of the somatotropin to the cow during the selected feeding period.

The somatotropin can be administered as a prolonged release dose, for example, as a dose is effective for at least 7 days or effective for at least 14 days. The conditions for delivering the somatotropin can comprise administering the somatotropin to the circulatory system of the cow.

Another method for enhancing milk production in a dairy cow, comprises the steps of feeding to the cow, during a selected period, a total dairy cattle feed ration in conjunction with the delivery of an effective amount of a biologically active somatotropin to the cow.

The feed ration comprises a forage component and a feed composition. The forage component comprises from about 20% to about 60% of the ration, and has from about 20% to about 100% corn silage produced from $F_1$ hybrid corn plants homozygous for bm3. The silage has an in vitro neutral detergent fiber digestibility of about 44% to about 60% and a whole plant in vitro digestibility of from about 65% to about 85%. The ration has a fiber content of about 20% to about 40%. In certain embodiments, in vitro neutral detergent fiber digestibility is from 44% to about 55% and the whole plant in vitro digestibility is from about 74% to about 80%.

The biologically active somatotropin is administered to the cow under conditions delivering an effective amount of the somatotropin to the cow during the selected feeding period.

Another method for enhancing milk production in a dairy cow, comprises the step of feeding to the cow a total dairy cattle feed ration. The ration comprises a combination of a forage component and a feed composition. The forage component comprises from about 20% to about 60% of the ration. The forage component comprises from about 20% to about 100% corn silage produced from $F_1$ hybrid corn plants homozygous for bm3. The silage has an in vitro neutral detergent fiber digestibility of about 44% to about 60% and a whole plant in vitro digestibility of from about 65% to about 85%. The ration has a fiber content of about 20% to about 40%. In some embodiments, the in vitro neutral detergent fiber digestibility is from 44% to about 55% and the whole plant in vitro digestibility is from about 74% to about 80%.

DESCRIPTION OF THE PREFERRED EMBODIMENTS

A feed ration has been discovered that comprises a corn silage produced from corn plants exhibiting a brown midrib phenotype. Such a ration can be fed to ruminants such as beef cattle and dairy cattle; feeding of such silage to dairy cattle results in unexpected improvements in milk production.

A silage component is produced from corn plants displaying the brown midrib phenotype. This phenotype is exhibited by plants homozygous for a mutant allele at either the bm1, bm2, bm3 or bm4 locus. In some embodiments, such plants may display the brown midrib phenotype due to homozygosity at more than one of the bm loci. Mutant bm alleles are known to reduce and alter the lignin content in plants homozygous for such alleles. The lignin content may be reduced 20%, 30%, or up to about 45% compared to corn of the same genetic background but having a wild-type Bm gene.

Corn inbreds and hybrids carrying bm alleles and displaying the bm phenotype may be produced by corn breeding methods known in the art. In one embodiment, a corn inbred line is converted to the bm phenotype in a breeding program initiated from the $F_1$ progeny of a cross between a plant of a first inbred (wild-type for the bm phenotype) and plants of a second line carrying the desired bm allele. $F_1$ plants are backcrossed to the first inbred line until an inbred line is obtained that has substantially the same genotype as the original inbred line except for the replacement of the wild-type Bm gene by the mutant bm gene.

In another embodiment, a pedigree breeding program may be used in which two inbreds, one of which carries the bm phenotype, are crossed and new, unique inbreds are selected that carry desired yield and agronomic performance characteristics as well as the bm phenotype. Conversion programs, pedigree breeding programs, breeding programs using synthetics and other methods for obtaining bm inbreds are known in the art. See, e.g., Hallauer, et al. in Corn and Corn Improvement, Sprague et al., eds. pp. 463–564 (1988).

In addition to selecting and identifying plants containing a mutant bm gene, it is desirable to select concomitantly for plants having superior agronomic and yield performance characteristics.

Techniques for identifying plants displaying the brown midrib phenotype are known in the art. For example, the underside of leaves may be examined at 10–14 days before tassel emergence (4–6 leaf stage, 2–3 ft. height) for the appearance of a golden-brown or reddish-brown color on the midrib. Plants may also be examined at maturity by removing a leaf sheath and examining the stalk. The stalk has a golden-brown or reddish-brown color if the brown midrib phenotype is expressed. Brown pigment is also present in the cob and in the roots. Because the bm phenotype is recessive, the presence of the bm gene in heterozygotes can be determined by performing a self and evaluating the selfed progeny for the expected 3:1 segregation ratio. Alternatively, marker-assisted breeding techniques may be used, e.g., restriction fragment length polymorphisms (RFLP), simple sequence repeats (SSR), microsatellite markers or PCR markers. Marker-assisted breeding techniques are useful, in that plants heterozygous for the bm allele can be identified without the necessity for evaluating phenotypic ratios in selfed progeny.

Once inbreds having the bm phenotype and desired performance characteristics have been identified, each inbred is evaluated for the development of appropriate hybrid combinations by test crosses or top crosses to another inbred displaying the bm phenotype.

Suitable hybrids are selected to have certain desirable agronomic characteristics. Such characteristics include, for example, satisfactory disease resistance or tolerance, satisfactory insect resistance or tolerance and satisfactory seedling vigor. Such general characteristics are desired in all types of corn hybrids regardless of the intended use of the hybrid; the best available performance with respect to these characteristics will be incorporated into a bm hybrid. Methods and tests for identifying inbreds having the desired general agronomic performance characteristics in hybrid combination are known in the art.

In addition, hybrids are developed that are adapted for use in short, medium or long growing seasons according to a relative maturity rating system such as the Minnesota Maturity Rating (MMR). See, e.g., U.S. Pat. No. 5,495,067, incorporated herein by reference.

However, certain other characteristics are of particular relevance in selecting suitable bm inbreds and hybrids. One relevant characteristic is the forage yield of the bm hybrid. The forage yield of a suitable bm hybrid is from about 20 to about 28 Tons per acre (adjusted to 70% moisture), preferably from about 22 Tons per acre to about 28 Tons per acre, more preferably from about 24 Tons per acre to about 28 Tons per acre. The forage yield can be from about 25 Tons/acre to about 32 Tons/acre in newer hybrids that are converted to express the bm phenotype.

A bm hybrid typically has a decrease in forage yield compared to the forage yield of its isogenic counterpart lacking the bm phenotype. However, preferred bm hybrids have a forage yield decrease of less than 15% compared to their isogenic counterparts, preferably a decrease of about 10% or less.

Another relevant characteristic is the in vitro digestibility of corn silage made from a bm hybrid as determined after about 30 days of fermentation. In vitro digestibility can be measured by determining neutral detergent fiber digestibility (NDF Digestibility) using methods known in the art. See, e.g., Goering, H. and Van Soest, P., Forage Fiber analyses in Agriculture Handbook 379, U.S. Department of Agriculture, Washington, D.C., pp. 1–20 (1975). Neutral detergent fiber is a measure of the cellulose, hemicellulose and lignin fractions of silage and constitutes from about 35 percent to about 55 percent of the silage dry matter, generally from about 40 percent to about 50 percent. Preferred bm hybrids have an in vitro NDF digestibility of from about 44 percent to about 60 percent, preferably from about 44 percent to about 55 percent, more preferably from about 47 percent to about 53 percent. In some embodiments, the in vitro NDF digestibility is from about 44% to about 50%. The NDF digestibility of bm hybrids preferably is about 6 to about 15 percentage units greater than the corresponding isogenic normal hybrid (which is homozygous for Bm3).

In vitro digestibility can also be measured on the whole plant after about 30 days of fermentation. Whole plant in vitro digestibility is also referred to herein as dry matter digestibility or IVTD. Suitable hybrids have an IVTD value of from about 65% to about 85%, preferably from about 70% to about 85%, more preferably from about 74% to about 85%. In certain embodiments, the IVTD value of bm hybrids is from about 74 percent to about 80 percent. The IVTD value of a bm hybrid is about 2 to about 7 percentage units greater than the IVTD value of the corresponding isogenic normal hybrid.

In vitro NDF digestibility and IVTD can be measured, for example, by collecting fresh-cut plant material and ensiling it in mini-silo fermentation canisters. The material may be reshred prior to ensiling to provide more uniform fermentation. After about 30 days, the pH of the fermented material is stable and in vitro NDF Digestibility and IVTD are determined as described in Goering, H. and Van Soest, P., supra, except that a 30 hour digestion is performed rather than a 48 hour digestion.

The forage yields, IVCWD values and IVTD values of the novel bm hybrids disclosed herein are useful in determining the suitability of such hybrids for inclusion in a dairy cattle feed ration.

Examples of corn inbreds suitable for producing corn silage include, without limitation, inbreds AR5252bm3, 7675bm3, 7677bm3, AR5251bm3 and AR5651bm3. Corn seeds possessing a mutant bm allele are also available from various universities and seed stock centers. These seeds can also be used to initiate a bm breeding program.

An inbred line according to the invention preferably is homozygous for a bm3 allele. Certain bm3 alleles have been sequenced, e.g., the bm3-1 and bm3-2 alleles. Vignols et al. Plant Cell 7:407–416 (1995). Alleles that have a deletion, e.g., a deletion similar to that in bm3-2, are preferred because such alleles are less likely to revert to wild-type.

Once bm inbreds that provide the desired performance in hybrid combination have been identified, production of $F_1$ hybrid bm seed is undertaken. Typically, a substantially uniform assemblage of $F_1$ bm hybrid corn seeds is conditioned and bagged in packaging material by means known in the art to form an article of manufacture. Such a novel bag of seed has a package label accompanying the bag, e.g., a tag or label secured to the packaging material, a label printed on the packaging material or a label inserted within the bag. The package label indicates that the seeds therein are effective for producing silage that can be fed to dairy cattle. Preferably, the package label indicates that the resulting silage is to be combined with a feed composition component as disclosed herein. The package label may also indicate that silage resulting from seeds contained therein is effective for increasing milk production when fed to lactating cows as disclosed herein.

$F_1$ bm hybrid seed is planted and cultivated according to standard agronomic practices in the geographic area to which the hybrid is adapted. Growers typically take into account soil fertility, crop rotation practices and other factors specific to the locale in which the hybrid corn is being grown.

$F_1$ hybrid bm corn plants may be grown to maturity and the seeds produced thereon harvested for use as grain. However, above-ground parts of bm hybrid corn plants preferably are harvested after grain fill, but before drydown. Typically, plants are harvested using a mechanical forage harvester which chops the above-ground portion of the plant into small pieces. Harvesting typically is based on the stage of seed maturity and occurs about the stage at which the color line is halfway down the kernel. The precise harvest time will depend, of course, upon geographical location and seasonal factors such as the weather. The chopped material is then ensiled by techniques known in the art, e.g., in trenches or in concrete stave silos. Microbial inoculants and/or preservatives may be added to promote silage formation, if desired.

Corn silage from bm hybrids is fed to dairy cattle as a total dairy cattle feed ration (also referred to herein as a total mixed ration or total ration) comprising bm silage and a feed composition. The nutrient composition of the silage can be determined, e.g., percent dry matter, percent NDF, percent CP, in vitro NDF digestibility and IVTD. Based on this information, a total dairy cattle feed ration is formulated.

A feed composition component of the invention may be a complete feed form, a concentrate form, blender form or base mix form. By complete feed form it is meant that the feed represents the cows entire grain ration. By concentrate form it is meant that the feed will be used as the primary supplemental protein source and would normally be fed with grain to meet a cow's protein needs. By blender form it is meant that the feed will be mixed with approximately a 50:50 ratio with grain to form the complete grain ration. The base mix form is similar to the concentrate form, but is typically higher in protein content and is used at lower inclusion rates. The base mix form will be a primary, but often not the sole source of supplemental protein.

For example, a complete feed form composition may contain wheat middlings, corn, meat and bone meal, soybean meal, salt, macro-minerals, trace minerals and vitamins. Alternative or optional ingredients commonly include, but are not restricted to, fat, sunflower meal, feather meal, malt sprouts, distillers' grains, canola meal and soybean hulls. Other alternative or optional protein sources include, for example, blood meal, corn gluten meal, peanut meal, cottonseed meal, soybeans (extruded or roasted), wheat bran and high fat rice bran.

A concentrate form composition, a blender form composition or a base mix form composition can be prepared by those of skill in the art, based upon the complete feed composition discussed above. Grains fed with the blender, concentrate and base mix forms of the composition can include, but are not limited to, corn, barley, oats, millet, rice, sorghum and wheat. Intake of the total grain ration will typically range from 2.7 to about 17 kilograms (kg) per day.

A nutrient composition of total dairy cattle feed ration comprising bm silage contains crude protein (CP) at a relatively high level in order to increase milk production. On a dry matter basis, CP is about 17% or greater, preferably from about 18% to about 21%. If there are reproductive difficulties, the amount of CP may be reduced. About 30% to about 50% of the CP is soluble protein (also referred to as SP, degradable intake protein, or DIP), preferably about 35% to about 50%, more preferably about 40% to about 45%. A total ration having a CP level at the lower end of the range of values results in greater weight gain and smaller increases in milk production. On the other hand, a ration with a CP level at the upper end of the range of values results in smaller weight gains and greater increases in milk production. About 20% to about 40% of the CP in the total ration is rumen undegraded protein (RUP, undegradable intake protein, or UIP), preferably from about 25% to about 40%, more preferably from about 25% to about 35%.

The forage component in the ration typically constitutes about 20% to about 60% of the ration on a dry matter basis and is added to achieve a fiber content of about 20% to about 40%, preferably from about 25% to about 35%. These values are appropriate for cows in early lactation; mid-lactation cows may have a higher forage/concentrate ratio. The bm silage comprises from about 20% to about 100% of the forage on a dry matter basis, preferably from about 25% to about 90%, more preferably from about 40% to about 90%, most preferably from about 70% to about 90%. In a preferred embodiment, bm silage is present at about 80%. Although bm silage may comprise 100% of the forage component in a ration, higher amounts of a protein source such as soybean meal will need to be included; doing so increases the overall cost of the diet. Therefore, it can be more cost-effective to include bm silage at less than 100% of the forage component.

Sources that may be used to complete the forage component of the ration include, but are not limited to, corn silage from non-bm corn plants, alfalfa haylage, grass silages (e.g., sudangrass, orchardgrass or sorghum-based silage), grass hays (e.g., sudangrass or orchardgrass) and alfalfa or clover hay. Such other forages are known in the art.

The silage component and the feed composition component are combined and fed to dairy cattle under generally accepted dairy cow management conditions. Typical dairy cow management conditions include known measures for animal care, shelter and veterinary treatment, under lactation and gestation cycles used by dairy farmers. Under typical conditions for feeding and managing of lactating dairy cows, a total ration comprising bm silage and having a nutrient composition disclosed herein provides a significant increase in milk yield on a raw basis or fat-corrected basis, without adversely affecting general animal health, particularly live weight.

A total ration includes components such as fat, vitamins and minerals in proportions and within ranges that are known in the art. Maximum fiber digestibility occurs in a rumen environment suitable for growth of fiber-digesting organisms. Thus, the levels of other components are considered when formulating a total dairy cattle feed ration. For example, high levels of unsaturated fatty acids may depress NDF digestibility. In addition, the level of non-structural carbohydrate is adjusted to provide sufficient energy from starch fermentation without decreasing rumen pH to such an extent that the growth of fiber-digesting microbes is inhibited.

A method according to the invention comprises administration of a biologically active somatotropin to a dairy cow. Somatotropin refers to a peptide that has biological activity and chemical structure similar to those of somatotropin produced in the pituitary gland of an animal. Such somatotropins include, without limitation, natural somatotropins produced by pituitary somatotropic cells and somatotropins expressed by genetically transformed microorganisms such as *E. coli* or yeasts. Biologically active somatotropins may have an amino acid sequence identical to natural somatotropins or may be analogs having one or more alterations in amino acid sequence that provide enhanced biological activity or some other advantage. Illustrative embodiments of suitable somatotropins are described in, e.g., U.S. Pat. Nos. 4,693,973, 5,411,951, 5,037,806 and 5,086,041, all of which are incorporated herein by reference. A preferred somatotropin is bovine somatotropin.

Typically, somatotropin is administered parenterally, e.g., by intramuscular or subcutaneous injection, which delivers the peptide to the circulatory system. Suitable formulations for administering a somatotropin are known in the art. For example, somatotropin can be injected in a physiologically acceptable vehicle such as a wax and an oil. See, e.g., U.S. Pat. Nos. 4,977,140, 5,474,980, 5,156,851 and 5,013,713, all of which are incorporated herein by reference. In some embodiments, a prolonged release formulation is used, such that a dose of somatotropin effective for enhancing milk production over a period of several days is released into the circulatory system with a single administration, e.g., at least 7 days, at least 14 days or at least 21 days.

A biologically active somatotropin is administered under conditions that provide an amount of peptide effective for enhancing milk production to a cow. Techniques and means are known in the art for determining appropriate doses to be supplied or provided to an individual cow. Typically, amounts of somatotropin between about 5 and about 75 mg/cow/day are suitable for use in the invention. For example, parenteral administration of a single dose of about 300 mg of zinc-associated somatotropin can be sufficient to provide an increased amount of bovine somatotropin for a period of about 15 days. U.S. Pat. No. 5,086,041, incorporated herein by reference.

A feed ration comprising bm corn silage is fed during a selected period to at least one ruminant. Somatotropin is administered so that the production-enhancing effect of the peptide coincides with the feeding of the bm silage-containing ration. For example, a prolonged release formulation of somatotropin can be administered to a cow every 14 days over a 180 period. Concomitantly, a bm silage ration described above is fed daily to the cow over the same 180 day period. As an alternative, somatotropin can be administered daily and a bm silage ration can be fed daily. The somatotropin can be administered, e.g., by injection, either before or during the period in which the ration is being fed, provided that an effective amount of the peptide is delivered during the same period. The feeding period can be short, e.g., 4 days, or preferably longer, e.g., 10 days, 30 days or more.

A biologically active somatotropin may be administered to both primiparous and multiparous cows, either in early, mid or late lactation, e.g., about 63 to about 360 days postpartum. Somatotropin is particularly useful for increasing milk production during mid and late lactation; i.e., about 100 to about 360 days postpartum.

Feeding a dairy cattle feed ration comprising bm corn silage and coextensively supplying an effective amount of a biologically active somatotropin results in significant increases in milk production compared to the increase observed with somatotropin alone. An increase in milk production of at least about 1.8 kg/cow/day is observed. For example, an increase in milk production of about 3 kg/cow/day can be observed over a 4 day period. A method of administering a biologically active somatotropin and feeding a bm silage feed ration as disclosed herein provides significant utility to the producer because of such increases in milk production. Moreover, protein, lactose and solids-not-fat (SNF) components of milk are not altered significantly after feeding a bm silage total ration and administering somatotropin as disclosed herein.

The invention will be further understood with reference to the following illustrative embodiments, which are purely exemplary and should not be taken as limiting the true scope of the present invention as described in the claims.

EXAMPLE 1

Preparation of Silage from a Brown Midrib Hybrid

Inbred lines AR5152bm3 and AR5751bm3 are crossed (AR5152bm3×AR5751bm3) to make $F_1$ hybrid seed carrying the brown midrib genotype. Control hybrid seed is prepared by crossing the unconverted parental lines.

The control and bm hybrid seed is planted at a density of 24,900 kernels per acre and cultivated using a standard fertilization program. The corn is harvested 4 months after planting, using a forage harvester having a ⅛ in. theoretical length of cut (TLC) and a screen. The harvested material is placed in polyethylene bags (Ag Bags). If desired, the harvested material is treated with inoculant and/or preservative. The forage yield for bm corn silage is about 1 wet ton per acre less than the control hybrid corn.

Samples are collected from the polyethylene bags after 30 days of fermentation/storage and assayed for nutrient concentrations. Typical results are shown in Table 1. The control corn silage and the bm corn silage are similar in nutrient composition, except for fiber digestibility and $NE_L$ concentration. The greater $NE_L$ concentration is likely related to the in vitro digestibility of NDF, ADF, and hemicellulose.

TABLE 1

| Nutrient composition of corn silages[1] | | |
|---|---|---|
| Nutrient | Control | BMR |
| Dry matter, % | 34.6 | 31.9 |
| Crude protein, % | 8.18 | 8.58 |
| Fat, % | 2.74 | 2.59 |
| ADF, % | 18.76 | 19.93 |
| NDF, % | 38.20 | 40.67 |
| Hemicellulose, % | 19.44 | 20.74 |
| NDF dig., % | 52.4 | 65.3 |
| ADF dig., % | 43.5 | 60.9 |
| Hemicellulose dig., % | 60.9 | 69.5 |
| Ash, % | 3.34 | 3.63 |
| NFC, % | 47.54 | 44.53 |
| $NE_L$, Mcal/cwt. | 76.0 | 80.5 |
| Ca, % | .19 | .19 |
| P, % | .23 | .22 |
| Mg, % | .14 | .13 |
| K, % | 1.09 | 1.27 |
| Na, % | .01 | .09 |
| Salt, % | .22 | .13 |

[1]Nutrients are expressed on a dry matter basis.

EXAMPLE 2

Formulation of a Dairy Cattle Feed Ration

The following experimental diets are developed to be fed as a total mixed ration (TMR). The following assumptions are used in ration formulation: the early lactation experimental dairy cow is estimated to weigh 636 kg and to produce 50 kg of milk per day with 3.30% fat, 3.10% milk protein and no body weight change. Dry matter intake (DMI) is predicted to be slightly less than 4.0% of body weight. The TMR is formulated to contain on a dry matter basis: 50% complete feed mix, 33% corn silage and 17% alfalfa haylage. The ingredient composition of the complete feed is given in Table 2 and the nutrient composition of the complete feed mix is given in Table 3.

TABLE 2

| Ingredient Composition of Complete Feed[1] | |
|---|---|
| INGREDIENT | Composition (% by weight) |
| Corn, coarse ground | 38.7 |
| Wheat Middlings | 20.0 |
| Meat & Bone Meal (50% protein) | 1.5 |
| Hi Pro Soybean Meal (49% crude protein) | 1.9 |
| Feather Meal | 3.5 |
| Canola Meal | 20.0 |
| Animal fat | 2.3 |
| Minerals and Vitamins | 4.7 |
| Distillers grains | 7.4 |
| Total | 100.0 |

[1]As fed basis.

TABLE 3

| Nutrient Composition of Complete Feed | |
|---|---|
| NUTRIENT | COMPOSITION[1] |
| Dry Matter | 88.0 |
| Crude Protein (CP) | 23.0 |
| Soluble Protein (SP as % of CP) | 21.0 |
| RUP (% of CP) | 45.0 |
| Fat | 5.0 |
| Net Energy of Lactation ($NE_L$) Mcal/kg | 92.0 |
| Acid Detergent Fiber (ADF) | 9.3 |
| Neutral Detergent Fiber (NDF) | 19.5 |
| Non-Fiber Carbohydrate (NFC) | 43.0 |
| Calcium | 1.40 |
| Phosphorus | .90 |
| Magnesium | .45 |
| Sulfur | .50 |
| Salt | 1.50 |

[1]Percentages for nutrients given as % by weight on a dry matter basis

Brown midrib (BMR) or control corn silage (Example 2) are combined with complete feed mix and alfalfa haylage to form the rations, using each silage in an equal amount on a dry matter basis. Rations contain approximately 18.5% crude protein, 32% soluble protein and 40% rumen undegraded protein. Both rations are adjusted to a calculated pH of about 6.2 Both rations are balanced to meet or exceed mineral, vitamin and total bypass protein requirements.

EXAMPLE 3

Milk Production Using BMR Silage in a Dairy Cattle Ration 20 lactating dairy cows are utilized in a randomized complete block design experiment, consisting of 5 primiparous cows and 5 multiparous cows fed control silage and 5 primiparous cows and 5 multiparous cows fed BMR silage. Cows are randomly assigned after calving. During the fifth week postpartum, the cows are abruptly switched to the appropriate feeding ration and continued on that ration from week 5 to week 17 postpartum. Primiparous cows are producing more than 25 kg/day of milk during the 4th week postpartum. Multiparous cows are producing greater than 29.5 kg/day of milk during the 4th week postpartum. All cows are disease free and otherwise healthy. Cows are fed ad libitum for the duration of the experiment, twice daily at 12 hour intervals, if possible. Cows are fed to allow for 5 to 10% feed refusal. The dietary ration and percentages of complete feed mix (Example 2), corn silage (Example 1) and alfalfa haylage on a dry matter basis are given in Table 4.

Milk production is measured at each milking and reported daily. Two samples of milk are taken weekly from each cow for composition analysis, including fat, protein, lactose, solids-not-fat and somatic cell counts. Body weights are recorded weekly after calving. Body condition scores are recorded at approximately weeks 4, 8, 12 and 16 postpartum. The same employee records condition scores at each measurement time. Body conditions scores are recorded according to the definitions indicated in Table 5.

TABLE 4

Dietary feeding guidelines to feed concentrate mix and forages

| | Control ration | BNR ration | | Control ration | BMR ration |
|---|---|---|---|---|---|
| Ration Content | % of DM | % of DM | DM, % | % as Fed | % as Fed |
| Control Silage | 33.0 | — | 34.6 | 50.3 | — |
| BMR Silage | — | 33.0 | 31.9 | — | 52.4 |
| Complete Feed | 50.0 | 50.0 | 88.0 | 30.0 | 28.8 |
| Alfalfa Haylage | 17.0 | 17.0 | 45.6 | 19.7 | 18.9 |
| Total | 100.0 | 100.0 | | 100.0 | 100.0 |

The results indicate that cows fed BMR silage have a statistically significant increase in milk production when comparing unadjusted means or when comparing covariate adjusted means. The increase is from about 1.8 kg milk/cow/day to about 5.0 kg milk/cow/day. However, there is a statistically significant decrease in milkfat percentage in milk from cows fed the ration containing BMR silage.

Table 5

Instructions for Body Condition Scoring
Score Definition

1 Loin area has limited flesh covering, is prominent and the ends of spinous processes are sharp to touch. Definite overhanging shelf effect is visible. Individual vertebrae of the hind quarters are prominent and distinct. Hooks and pin bones are notable. The area below the tail-head and between pin bones is severely depressed causing the bone structure of the area to appear extremely sharp.

2 Individual spinous processes are usually discernible but are not prominent. Ends of processes are sharp to touch, although they have greater flesh covering. The processes do not have a distinct overhanging shelf effect. Individual vertebrae of the hind quarters are not visually distinct but are readily distinguishable by palpitation. Hooks and pin bones are prominent, but the depression between them is less severe. The area below the tail-head and between the pin bones is depressed, but the bone structure is not devoid of flesh covering.

3 Spinous processes are discernible by applying slight pressure. Area over processes appears smooth and the overhanging shelf effect is not noticeable. Vertebrae of the hindquarters appear as a rounded ridge. Hooks and pin bones are rounded and smooth. The area between the pin bones and around the tail-head appear smooth without sign of fat deposition.

4 Individual spinous processes can be distinguished only by firm palpitation. Processes appear flat or rounded with no overhanging shelf effect. The ridge formed by the vertebrae of the hindquarters is rounded and smooth, flattening out as you move forward. Hooks are rounded, and the span between hooks is flat. The area around the tail-head and pin bones is rounded with evidence of fat deposition.

5 Bone structure of the vertebral column, spinous processes, hooks and pin bone regions is not visually apparent. Evidence of fat deposition is prominent. The tail head appears to be buried in fatty tissue.

EXAMPLE 4

Development of bm Hybrids

Eleven bm hybrids were developed from inbreds homozygous for bm3. These hybrids were grown and ensued at six U.S. locations for 2 years and pairwise comparisons were made between each bm hybrid and the corresponding normal isogenic hybrid. The results for forage yield, IVTD and in vitro NDF digestibility are summarized in Table 6. Hybrids are listed in Table 6 according to their maturity rating. For example, hybrid number 2927 is a short season (95 day MMR) type, whereas 8177, 757 and 8427 and long season (115 day MMR) types.

The results indicate that $F_1$ bm hybrids can be developed whose silage has an NDF digestibility of 47% or greater. The results also show that bm hybrids can be developed and adapted that have an IVTD of 75% or greater and a forage yield that is only 3–15% less than the yield of the isogenic normal hybrid. For example, hybrid 5327 has a 105 day maturity rating and an average NDF dig. of 51.78%, yet has a forage yield of 25.59 tons/acre. Hybrid 757 has a 115 day maturity rating and an average NDF dig. of 47.88%, yet has a forage yield of 27.00 tons/acre. Moreover, these results indicate that bm hybrids derived from different heterotic groups and adapted to different maturities can be developed. Silage from such bm hybrids is suitable for feeding to cattle as disclosed herein.

TABLE 6

Pairwise Comparisons of Silage from 13 bm Hybrids and Isogenic Normal Hybrids[a,c]

| Hybrid No. | % CP bm | % CP Normal | IVTD(%) bm | IVTD(%) Normal | NDF dig. (%) bm | NDF dig. (%) Normal | % NDF bm | % NDF Normal | Forage Yield (Tons/Acre at 70% Moisture) bm | Forage Yield (Tons/Acre at 70% Moisture) Normal | Yield Decrease[b] | Inbred Parents for bm Hybrid[d] Female | Inbred Parents for bm Hybrid[d] Male |
|---|---|---|---|---|---|---|---|---|---|---|---|---|---|
| 2977 | 8.51 | 8.23 | 77.06* | 74.50 | 49.60* | 40.88 | 45.48 | 43.14 | 20.13* | 25.45 | 21 | AR5151bm3 | AR5551bm3 |
| 4227 | 8.95 | 7.83 | 78.03* | 73.05 | 50.99* | 38.20 | 44.81 | 43.52 | 22.35 | 23.05 | 3 | AR5154bm3 | AR5751bm3 |
| 4277 | 7.46 | 7.61 | 77.32 | 73.90 | 48.35 | 42.32 | 43.88 | 45.22 | 23.72 | 26.01 | 9 | AR5252bm3 | AR5551bm3 |
| 4327 | 7.88 | 7.26 | 76.88* | 74.04 | 47.99* | 41.37 | 44.36 | 44.44 | 23.21* | 30.35 | 24 | AR5253bm3 | AR5551bm3 |
| 5327 | 8.20 | 7.72 | 78.71 | 76.81 | 51.78* | 42.15 | 44.07 | 40.06 | 25.59 | 29.00 | 12 | AR5152bm3 | AR5551bm3 |
| 6127 | 8.55 | 8.23 | 78.22* | 73.47 | 50.30* | 41.37 | 45.03 | 45.25 | 24.39 | 25.67 | 5 | AR5154bm3 | AR5655bm3 |
| 657 | 8.92 | 8.29 | 78.75* | 73.26 | 50.99* | 40.64 | 43.56 | 45.08 | 25.00 | 27.49 | 9 | AR5252bm3 | 7675bm3 |
| 6227 | 8.93 | 8.22 | 78.33* | 73.76 | 50.86* | 40.28 | 44.41 | 44.26 | 24.76 | 26.17 | 5 | AR5152bm3 | 7675bm3 |
| 6337 | 9.28 | 8.62 | 78.58* | 74.33 | 48.43* | 38.08 | 41.54 | 41.90 | 24.87* | 29.36 | 15 | AR5252bm3 | AR5751bm3 |
| 6727 | 8.87 | 8.74 | 78.28* | 73.86 | 49.79* | 38.87 | 43.52 | 42.82 | 25.13 | 26.45 | 5 | AR5152bm3 | AR5751bm3 |
| 8177 | 8.13 | 7.32 | 76.86* | 71.91 | 48.35* | 41.02 | 45.27 | 47.89 | 25.72 | 30.17 | 15 | AR5152bm3 | AR5655bm3 |
| 757 | 8.49 | 8.12 | 76.65* | 71.79 | 47.88* | 39.89 | 44.96 | 46.97 | 27.00 | 30.23 | 11 | AR5252bm3 | 7677bm3 |
| 8427 | 8.24 | 8.28 | 76.41* | 71.77 | 49.85* | 40.54 | 47.27 | 47.64 | 25.33* | 29.62 | 14 | AR5152bm3 | 7677bm3 |

[a]Values with an asterisk are significantly different from isogenic normal silage at $p < 0.05$ (Student's t-test)
[b]Percent decrease in forage yield of bm silage relative to isogenic normal silage
[c]Summary over two years at 5 or 6 locations
[d]Corresponding isogenic normal inbreds were used to make the normal hybrids

EXAMPLE 5

Formulation of a Dairy Cattle Feed Ration

Control and bm $F_1$ hybrid seed of Example 1 was planted and cultivated in the Midwest United States using a standard agronomic practices. The corn was harvested approximately 5 months after planting, using standard corn silage harvesting methods. The harvested material was ensiled in 150T capacity concrete bunker silos. The harvested material was not treated with inoculant or preservative.

A subsample of each load was ensiled in a 4 inch diameter ×16 inch length PVC experimental silo fermentation canister. Each silo contained a ¼ inch×1 inch piece of copper tubing inserted into the sidewall. The tubing was covered with a rubber policeman having a slit that allowed fermentation gases to escape while preventing entry of ambient air. Each fresh-cut silage sample was packed tightly into a silo and allowed to ferment for 30 days at ambient temperatures (above freezing) before opening and assaying for nutrient concentrations.

The results of the nutrient concentration assays are shown in Table 7. In vitro NDF digestibility was measured as described in Goering, H. and Van Soest, P., supra, except that the fermentation period was 30 hours instead of 48 hours. The control corn silage and the BMR corn silage were similar in crude protein and NDF and differed in 30 hour in vitro NDF digestibility.

TABLE 7

Nutrient composition of corn silages[1]

| Nutrient | Control | BMR |
|---|---|---|
| Dry matter, % as fed | 33.5 | 30.2 |
| Crude protein, % | 8.35 | 8.68 |
| ADF, % | 21.02 | 21.08 |
| NDF, % | 40.38 | 42.02 |
| Hemicellulose, % | 19.36 | 20.94 |
| NDF dig., % | 36.8 | 45.3 |
| Ash, % | 3.76 | 4.24 |

[1]Nutrients and digestibility are expressed on a dry matter basis.

Experimental diets were developed to be fed as a total mixed ration (TMR), using the following assumptions: the early lactation experimental dairy cow was estimated to weigh 613.6 kg and to produce 45.45 kg of milk per day with 3.5% fat, 3.30% milk protein and a 0.18 kg/day increase in body weight. Dry matter intake (DMI) was predicted to be slightly less than 4.0% of body weight.

The two TMRs were formulated to contain 56% forage on a dry matter basis. The forage consisted of 4 parts corn silage (either normal or BMR) to 1 part alfalfa haylage on a dry matter basis. The TMR also contained soybean meal (SEM, 44% crude protein), high moisture corn, finely ground dry corn, whole linted cottonseeds, mineral and vitamins. The two diets were balanced to be isonitrogenous and varied only in the proportions of SBM and high moisture corn. Rations contained approximately 18.0% crude protein, 44% of which was soluble protein and 31% of which was rumen undegraded protein (rumen bypass protein). Both rations were balanced to meet or exceed mineral and vitamin requirements. The ingredient composition of the two rations is given in Table 8. The nutrient composition of the two rations is given in Table 9.

TABLE 8

Ingredient Composition of Total Mixed Ration[1]

| INGREDIENT | Normal Silage (% by weight) | BMR Silage (% by weight) |
|---|---|---|
| Corn silage | 44.6 | 44.6 |
| Alfalfa silage | 11.2 | 11.2 |
| Soybean Meal (44% protein) | 19.2 | 18.8 |
| Corn, high moisture | 8.8 | 9.2 |
| Corn, dry ground | 5.6 | 5.6 |
| Cottonseeds, whole linted | 5.6 | 5.6 |
| Minerals and Vitamins | 5.0 | 5.0 |
| Total | 100.0 | 100.0 |

[1]Dry matter basis.

TABLE 9

Nutrient Composition of Total Mixed Ration[1]

| NUTRIENT | Normal Silage | BMR Silage |
|---|---|---|
| Dry Matter | 46.8 | 43.8 |
| Crude Protein (CP) | 18.0 | 18.0 |
| Soluble Protein (SP as % of CP) | 43.8 | 44.2 |
| RUP (RUP as % of CP) | 31.0 | 31.0 |
| Fat | 3.8 | 3.8 |
| Net Energy of Lactation (NE$_L$)[2] Mcal/kg | 1.72 | 1.72 |
| Acid Detergent Fiber (ADF) | 18.4 | 18.5 |
| Neutral Detergent Fiber (NDF) | 30.6 | 31.3 |
| Non-Fiber Carbohydrate (NFC) | 39.6 | 38.8 |
| Calcium | 1.01 | 1.01 |
| Phosphorus | 0.45 | 0.45 |
| Magnesium | 0.29 | 0.29 |
| Sulfur | 0.22 | 0.22 |
| Salt | 0.76 | 0.76 |

[1]Percentages for nutrients given as % by weight on a dry matter basis. Dry matter is given as % by weight of ration as fed.
[2]Book values (1.67 Mcal/kg) used for corn silage.

EXAMPLE 6

Milk Production Using BMR Silage in a Dairy Cattle Ration 32 lactating dairy cows were utilized in a complete block design experiment, consisting of 2 primiparous cows and 14 multiparous cows fed a ration containing control silage and 2 primiparous cows and 14 multiparous cows fed BMR silage. Cows within blocks were randomly assigned to treatments. All cows were disease free and otherwise healthy. Rations were formulated as described in Example 5.

The experiment was a crossover design with 28 day periods. The first 21 days of the period were used for diet adjustment and the last 7 days were used for data collection. Cows ranged from approximately 22 to 141 days in milk, averaging 90 days in milk at the beginning of the experiment.

Cows were milked 3 times daily. Milk production was measured at each milking and reported daily. Nine samples of milk were taken on 3 different days from each cow for composition analysis in each collection period. Composition analysis included fat, protein, lactose, and somatic cell counts. Composition analysis was carried out using Near Infrared Spectroscopy at the Michigan Dairy Herd Improvement Association, East Lansing, MI. Body weights were recorded on 2 consecutive days before the experiment started and on the last 2 days of each data collection period. Body condition scores were recorded on the day before the experiment started and on the last day of each data collection period. Scores were recorded according to the definitions indicated in Table 5. Three individuals recorded condition scores at each measurement time.

After 28 days, cows were abruptly switched from one ration to the other ration (from ration containing BMR silage to ration containing control silage and vice versa). Cows were fed and milked in the same manner as prior to the switch in ration. Milk was weighed and analyzed in the same manner as prior to the switch in ration. The experiment was terminated after 56 days. Data were analyzed using the fit model procedure in the JMP computer statistics program (SAS Institute, North Carolina).

The milk production results are shown in Table 10. The results indicate that cows fed BMR silage have a statistically significant increase in milk production when comparing treatment means. The increase was more than 2.7 kg of milk/cow/day on an uncorrected basis and about 2.6 kg milk/cow/day on a solids-corrected basis (Table 10, lines 2 and 5). There was no significant change in the percentage milk fat, protein, lactose, or solids-not-fat (SNF) between milk from cows fed control or BMR silage (Table 10, lines 6–9).

Dry matter intake (DMI) by cows fed BMR silage was significantly greater than that of cows fed control silage (Table 10, line 1). It is noteworthy that there was no significant difference in mean milk production for the two rations when dry matter intake (DMI) was used a covariate (P=0.42). This result suggests that increased milk production is due to an increase in the amount of total ration consumed per day when BMR silage was fed, i.e., that the rate of intake and feed conversion was increased.

Because milk from BMR silage-fed cows has a composition similar to that of milk from control silage-fed cows, milk from BMR-fed cows can be pooled with milk from other sources and processed by standard techniques. Moreover, milk from BMR silage-fed cows typically will not be subject to a price penalty due to non-standard component concentrations.

The effect of a ration comprising BMR silage on body condition and weight is shown in Table 11. Feeding of such a ration resulted in a greater weight gain than did feeding of a ration comprising control silage, although this difference was not statistically significant. Moreover, the body condition score change was significantly better when cows were fed BMR silage than when cows were fed control silage (P=0.049; Table 11). These results indicate that not only does feeding of a ration comprising BMR silage as disclosed herein increase milk production, cows fed such a ration have improved body condition scores. Improved body condition scores are a general measure of a cow's ability to sustain milk production over an extended period of time, e.g., multiple lactations.

TABLE 10

Milk Production

| Component | Control Silage | BMR Silage | P Value |
|---|---|---|---|
| Dry Matter Intake (DMI)[e] | 23.5 | 25.5 | <0.0001 |
| Milk Yield[c] | 39.0 | 41.7 | 0.002 |
| 4% FCM[a] | 35.7 | 38.0 | 0.0005 |
| 3.5% FCM[f] | 38.5 | 41.0 | 0.0005 |
| Solids Corrected Milk[g] | 35.2 | 37.8 | 0.0001 |
| Milk Fat (%)[d] | 3.46 | 3.43 | 0.71 |
| Milk Protein (%) | 2.95 | 2.99 | 0.35 |
| Milk Lactose (%) | 4.85 | 4.90 | 0.22 |
| SNF[b] (%) | 8.52 | 8.59 | 0.13 |
| Milk Fat (kg/cow/day) | 1.33 | 1.42 | 0.01 |
| Milk Protein (kg/cow/day) | 1.14 | 1.24 | 0.0001 |
| Milk Lactose (kg/cow/day) | 1.88 | 2.04 | 0.0005 |

[a]Milk yield on a fat-corrected basis to 4% milkfat. (Milk × 0.4) + (lbs. fat × 15.0). lbs fat = Milk × fat content.
[b]Percentage of Solids-not-fat.
[c]Milk production is expressed as kg/cow/day, unless indicated otherwise.
[d]Dry matter intake is expressed a kg per cow per day.
[e]Milk components are expressed as a percentage (gm/100 ml of milk), unless indicated otherwise.
[f]Milk yield on a fat-corrected basis to 3.5% milkfat. (Milk × 0.4255) + (16.425 × Fat content/100 × milk).
[g]Tyrrell, H. F. and J. J. Reid, J. Dairy Sci. 48.1215 (1965).

TABLE 11

Effect of BMR Silage on Body Condition and Weight Change

| Component | Control Silage | BMR Silage | P Value |
|---|---|---|---|
| Body Weight Change (kg increase after 28 days) | 2.2 | 4.76 | 0.45 |
| Body Condition Score Change after 28 days | 0.019 | 0.110 | 0.049 |
| Ratio: 4% FCM/DMI | 1.52 | 1.48 | 0.23 |

EXAMPLE 7

Milk Production Using a BMR Silage Ration and Bovine Somatotropin

An on-farm herd of about 80 lactating dairy cows was utilized to determine the effect of feeding BMR silage in combination with bovine somatotropin (BST) treatment. Cows were fed in a switchback trial, consisting of feeding a control ration for the first phase, feeding a BMR ration for the second phase, followed by a return to a control ration.

BMR corn hybrid 657bm3 (Table 6), produced from a cross of inbreds AR5252bm3×7675bm3, was grown and harvested for silage at the half milk line stage, using typical commercial farm practices. The material was ensiled for about 75 days in an outdoor environment before feeding. The nutrient composition of the silage was similar to that shown in Table 6. Control silage from a locally adapted normal hybrid was grown and harvested in the same manner.

Experimental diets were developed to be fed as a total mixed ration (TMR), assuming a dairy cow 100 days in milk, weighing 613.6 kg and producing 45.45 kg of milk per day with 3.9% fat, 3.30% milk protein. No increase in body weight was predicted. Dry matter intake (DMI) was predicted to be slightly greater than 4.0% of body weight.

The TMRs were formulated to contain about 46–47% forage on a dry matter basis. The forage consisted of approximately equal parts corn silage (normal or BMR) and alfalfa haylage on a dry matter basis. The TMRs also contained heated soybean flakes, high moisture corn, whole linted cottonseeds, and Gro-Mark(tm) Pro-Barley Mix, a proprietary mixture believed to comprise grain, minerals and vitamins. The TMRs were balanced to be isonitrogenous and to meet or exceed mineral and vitamin requirements. Rations contained slightly more than 18% crude protein, about 31–32% of which was soluble protein. The ingredient composition and the nutrient composition of the total mixed rations is given in Tables 12–13.

About 75% of the cows in the herd were treated with BST during the trial. BST was not administered to cows less than 30 days in milk nor to cows not confirmed to be pregnant; such cows constituted about 25% of the herd. BST (Posilac (tm), Monsanto, St. Louis, Mo.) was administered according to the manufacturer's instructions, using dosages recommended by the manufacturer.

TABLE 12

Ingredient Composition of Total Mixed Ration[1]

| | TMR[2] | | |
|---|---|---|---|
| INGREDIENT | Days 1–10 (Control Silage) | Days 11–21 (BMR Silage) | Days 22–31 (Control Silage) |
| Corn silage | 22.57 | 21.52 | 22.16 |
| Alfalfa silage | 24.90 | 25.79 | 23.76 |
| Soybean Flakes, heated | 2.60 | 3.00 | 3.94 |
| Corn, high moisture | 25.05 | 24.92 | 25.36 |
| Cottonseeds, whole linted | 4.60 | 4.59 | 4.66 |
| Gro-Mark (TM) ProBarley Mix | 20.28 | 20.18 | 20.13 |
| Total | 100.0 | 100.0 | 100.0 |

[1]Dry matter basis.
[2]% by weight.

TABLE 13

Nutrient Composition of Total Mixed Ration[1]

| | TMR | | |
|---|---|---|---|
| NUTRIENT | Days 1–10 | Days 11–21 | Days 22–31 |
| Dry Matter | 51.62 | 48.58 | 55.41 |
| Crude Protein (CP) | 18.58 | 18.53 | 18.16 |
| Soluble Protein (SP as % of CP) | 32.42 | 32.05 | 30.82 |
| Crude Fat | 5.59 | 5.56 | 5.83 |
| Net Energy of Lactation ($NE_L$)[2] Mcal/kg | 1.72 | 1.72 | 1.74 |
| Acid Detergent Fiber (ADF) | 18.87 | 18.70 | 18.50 |
| Neutral Detergent Fiber (NDF) | 29.43 | 28.92 | 28.81 |
| Calcium | 1.08 | 1.10 | 1.05 |
| Phosphorus | 0.57 | 0.57 | 0.56 |
| Magnesium | 0.34 | 0.35 | 0.34 |
| Sulfur | 0.26 | 0.26 | 0.26 |
| Salt | 0.56 | 0.55 | 0.55 |

[1]Percentages for nutrients given as % by weight on a dry matter basis. Dry matter is given as % by weight of ration as fed.
[2]Book values (1.67 Mcal/kg) used for corn silage.

Cows ranged from approximately 7 to 489 days in milk, averaging about 211 days in milk at the beginning of the experiment. Cows were milked twice daily. Milk production for the herd was measured at each milking. Cows were fed and milked in the same manner throughout the experiment. On day 1 of the trial, selected cows were treated with BST and the herd was placed on control ration (containing control silage). The herd was abruptly switched from control ration to BMR ration (containing BMR silage) on day 11. On the same day, selected cows were injected with BST. At day 22, cows were abruptly returned to the control ration. At day 25, selected cows were injected with BST.

Figure 1:
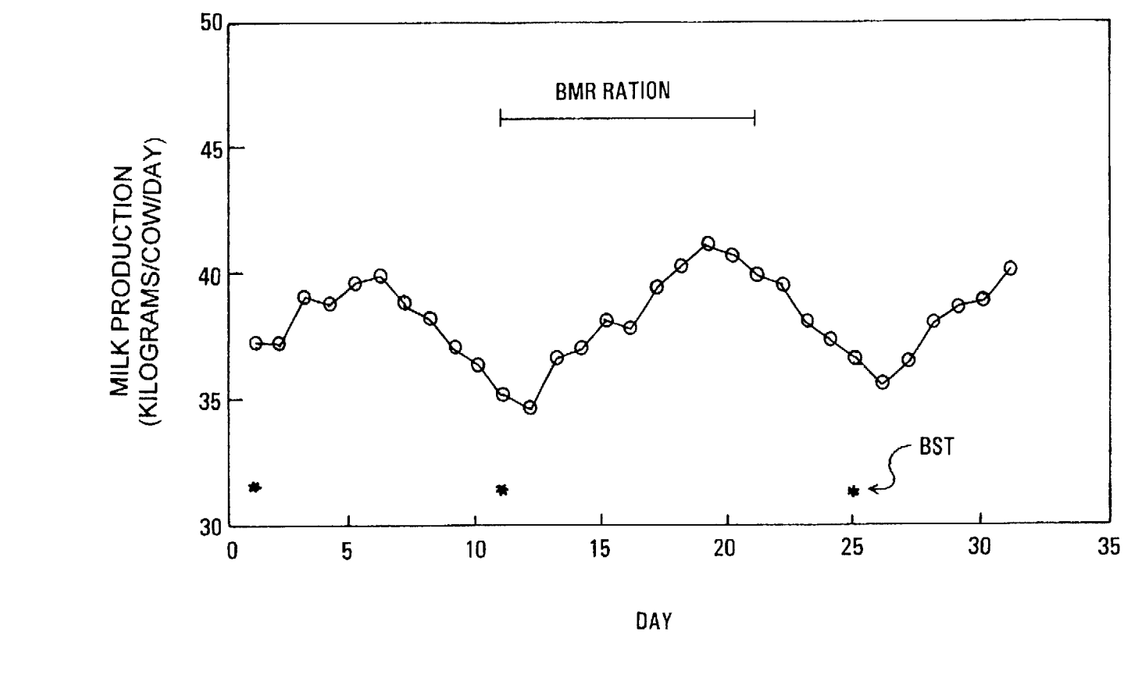
FIG. 1 shows herd milk production on a daily basis in a switchback trial in which normal or BMR silage was fed in conjunction with bovine somatotropin administration.

Herd milk production results are shown in Table 14 and presented graphically in FIG. 1. When the herd was fed a control feed ration, average daily milk production of the herd began to increase following treatment of selected cows with EST. Daily milk production peaked about 5–6 days at about 39 kg/cow/day and then declined to about 36 kg/cow/day. A peak in milk production between injections is typical of prolonged release EST administration.

The herd was switched to a ration comprising BMR silage at day 11. In the second phase of the trial, average milk production increased to about 39–40 kg/cow/day at 6 days after the EST treatment and ration change. Milk production remained at about 39–40 kg/cow/day for the duration of this phase of the trial. These results show that delivery of BST to cows in conjunction with the feeding of a ration comprising BMR silage results in a sustained increase in average daily milk production rather than the decline in milk production typically observed when BST treatment alone is used.

The sustained increase in milk production during the BMR ration phase is also shown by comparing the average daily milk production for the last four days of each phase. Average milk production for the last 4 days of the first phase (control ration/BST) was 37.50 kg of milk/cow/day on an uncorrected basis. Average milk production for the last 4 days of the second phase (BMR ration/BST) was 40.45 kg of milk/cow/day on an uncorrected basis.

TABLE 14

Milk Production With BMR and BST

| Diet | Trial Day | Cows Tested | Cows Milked | TMR Mix (kg) Morn | TMR Mix (kg) Eve | Milk Production (kg) Tank Weight | Milk Production (kg) Avg/Cow |
|---|---|---|---|---|---|---|---|
| Control | 1[a] | 73 | 69 | 1636 | 1636 | 2568 | 37.22 |
| | 2 | 73 | 69 | 1636 | 1636 | 2566 | 37.18 |
| | 3[b] | 71 | 66 | 1636 | 1636 | 2580 | 39.10 |
| | 4 | 71 | 66 | 1636 | 1636 | 2556 | 38.73 |
| | 5 | 71 | 66 | 1636 | 1636 | 2612 | 39.57 |
| | 6[c] | 70 | 67 | 1636 | 1636 | 2670 | 39.86 |
| | 7 | 70 | 67 | 1636 | 1636 | 2600 | 38.80 |
| | 8 | 70 | 67 | 1636 | 1636 | 2556 | 38.15 |
| | 9[d] | 69 | 66 | 1636 | 1636 | 2444 | 37.02 |
| | 10[e] | 70 | 67 | 1636 | —[f] | 2433 | 36.31 |
| BMR | 11[g] | 72 | 67 | 1818 | 1818 | 2357 | 35.18 |
| | 12[h] | 73 | 70 | 1818 | 1750 | 2422 | 34.60 |
| | 13 | 73 | 70 | 1818 | 1750 | 2560 | 36.58 |
| | 14 | 73 | 70 | 1750 | 1750 | 2587 | 36.95 |
| | 15 | 73 | 70 | 1818 | 1818 | 2666 | 38.09 |
| | 16[i] | 73 | 71 | 1818 | 1886 | 2682 | 37.77 |
| | 17 | 73 | 71 | 1841 | 1832 | 2796 | 39.39 |
| | 18[j] | 71 | 69 | 1836 | 1818 | 2774 | 40.20 |
| | 19 | 71 | 69 | 1818 | 1827 | 2836 | 41.10 |
| | 20[k] | 70 | 68 | 1809 | 1823 | 2763 | 40.64 |
| | 21 | 70 | 68 | 1827 | 1850 | 2710 | 39.84 |
| Control | 22 | 70 | 68 | 1682 | 1673 | 2682 | 39.44 |
| | 23 | 70 | 67 | 1682 | 1682 | 2545 | 37.99 |
| | 24 | 70 | 67 | 1682 | 1682 | 2500 | 37.31 |
| | 25[l] | 70 | 67 | 1591 | 1609 | 2450 | 36.56 |
| | 26[m] | 70 | 67 | 1600 | 1591 | 2381 | 65.54 |
| | 27 | 70 | 67 | 1591 | 1609 | 2442 | 36.45 |
| | 28 | 70 | 67 | 1595 | 1595 | 2545 | 37.99 |
| | 29 | 70 | 67 | 1559 | 1550 | 2585 | 38.58 |
| | 30[n] | 69 | 66 | 1555 | 1545 | 2563 | 38.84 |
| | 31 | 69 | 66 | 1568 | 1550 | 2642 | 40.03 |

[a]BST Injection; [b]2 Dry; 1 Mastitis; [c]2 Fresh; 1 Dry; [d]1 Died; 1 Sick; [e]1 Fresh; [f]Not Determined; [g]BST Injection; [h]2 Fresh; [i]Off-feed; [i]1 Fresh; [j]1 Displaced Abomasum (DA) Surgery; 1 Dry; [k]1 Dry; [l]BST Injection; [m]1 DA Surgery; [n]1 Dry To the extent not already indicated, it will be understood by those of ordinary skill in the art that any one of the various specific embodiments herein described and illustrated may be further modified to incorporate features shown in other of the specific embodiments.

The foregoing detailed description has been provided for a better understanding of the invention only and no unnecessary limitation should be understood therefrom as some modifications will be apparent to those skilled in the art without deviating from the spirit and scope of the appended claims.

What is claimed is:

1. A method for enhancing milk production in a dairy cow, comprising the steps of:

a) feeding to said cow, during a selected period, a total dairy cattle feed ration comprising a combination of:

a forage component comprising from about 20% to about 60% of said ration, said forage component comprising from about 20% to about 100% corn silage produced from $F_1$ hybrid corn plants homozygous for bm3, said silage having an in vitro neutral detergent fiber digestibility of about 44% to about 60%; and a feed composition, said ration having a fiber content of about 20% to about 40% and a crude protein content of from about 17% to about 21% on a dry matter basis, wherein about 30% to about 50% of said crude protein is soluble protein; and b) administering a biologically active somatotropin to said cow under conditions delivering an effective amount of said somatotropin to said cow during said selected period.

2. The method of claim 1, wherein said in vitro neutral detergent fiber digestibility is from about 6% to about 15% greater than the in vitro neutral detergent fiber digestibility of isogenic normal corn silage.

3. The method of claim 1, wherein said forage component comprises from about 40% to about 60% of said ration, and said bm3 corn silage comprises from about 40% to about 80% of said forage component.

4. The method of claim 3, wherein said forage component comprises from about 45% to about 55% of said ration and said bm3 corn silage comprises from about 50% to about 80% of said forage component.

5. The method of claim 1, said silage further having a whole plant in vitro digestibility of from about 65% to about 85%.

6. The method of claim 5, wherein said in vitro neutral detergent fiber digestibility is from about 44% to about 55% and said whole plant in vitro digestibility is from about 74% to about 80%.

7. The method of claim 1, wherein said somatotropin is administered as a prolonged release dose.

8. The method of claim 7, wherein said dose is effective for at least 7 days.

9. The method of claim 7, wherein said dose is effective for at least 14 days.

10. The method of claim 1, wherein said conditions comprise delivering said somatotropin to the circulatory system of said cow.

11. A method for enhancing milk production in a dairy cow, comprising the steps of:

a) feeding to said cow, during a selected period, a total dairy cattle feed ration comprising a combination of:

a forage component comprising from about 20% to about 60% of said ration, said forage component comprising from about 20% to about 100% corn silage produced from $F_1$ hybrid corn plants homozygous for bm3, said silage having an in vitro neutral detergent fiber digestibility of about 44% to about 60% and a whole plant in vitro digestibility of from about 65% to about 85%; and a feed composition, said ration having a fiber content of about 20% to about 40%; and b) administering a biologically active somatotropin to said cow under conditions delivering an effective amount of said somatotropin to said cow during said selected period.

12. The method of claim 11, wherein said in vitro neutral detergent fiber digestibility is from about 44% to about 55% and said whole plant in vitro digestibility is from about 74% to about 80%.

13. The method of claim 11, wherein said in vitro neutral detergent fiber digestibility is from about 6% to about 15% greater than the in vitro neutral detergent fiber digestibility of isogenic normal corn silage.

14. The method of claim 11, wherein said forage component comprises from about 40% to about 60% of said ration, and said bm3 corn silage comprises from about 40% to about 80% of said forage component.

15. The method of claim 14, wherein said forage component comprises from about 45% to about 55% of said ration and said bm3 corn silage comprises from about 50% to about 80% of said forage component.

16. The method of claim 11, wherein said somatotropin is administered as a prolonged release dose.

17. The method of claim 16, wherein said dose is effective for at least 7 days.

18. The method of claim 16, wherein said dose is effective for at least 14 days.

19. The method of claim 11, wherein said conditions comprise delivering said somatotropin to the circulatory system of said cow.

* * * * *

UNITED STATES PATENT AND TRADEMARK OFFICE
CERTIFICATE OF CORRECTION

PATENT NO.   : 5,767,080

DATED        : June 16, 1998

INVENTOR(S)  : James F. Beck, Dale H. Storck, and David P. Casper

It is certified that error appears in the above-identified patent and that said Letters Patent is hereby corrected as shown below:

Column 12, line 42, delete the second occurrence of "and" and insert --are--

Column 18, line 57, delete "EST" and insert --BST--

Column 18, line 60, delete "EST" and insert --BST--

Column 18, line 64, delete "EST" and insert --BST--

Signed and Sealed this

Fifteenth Day of December, 1998

Attest:

BRUCE LEHMAN

*Attesting Officer*    *Commissioner of Patents and Trademarks*